(12) United States Patent
Dubowski et al.

(10) Patent No.: US 8,709,708 B2
(45) Date of Patent: Apr. 29, 2014

(54) QUANTUM DOT TEMPLATE FOR FAST AND SIMULTANEOUS DETECTION OF DIFFERENT INFECTIOUS AGENTS

(75) Inventors: Jan J. Dubowski, Sherbrooke (CA); Ximing Ding, Mississauga (CA); Eric H. Frost, Sherbrooke (CA); Emanuel Escher, Sherbrooke (CA)

(73) Assignee: Societe de Commercialisation des Produits de la Recherche Appliquee SOCPRA-Sciences et Genie S.E.C., Sherbrooke, Quebec (CA)

( * ) Notice: Subject to any disclaimer, the term of this patent is extended or adjusted under 35 U.S.C. 154(b) by 1394 days.

(21) Appl. No.: 11/908,223

(22) PCT Filed: Mar. 10, 2006

(86) PCT No.: PCT/CA2006/000367
§ 371 (c)(1),
(2), (4) Date: May 29, 2008

(87) PCT Pub. No.: WO2006/094408
PCT Pub. Date: Sep. 14, 2006

(65) Prior Publication Data
US 2008/0261828 A1      Oct. 23, 2008

Related U.S. Application Data

(60) Provisional application No. 60/659,872, filed on Mar. 10, 2005.

(51) Int. Cl.
*B82Y 15/00*      (2011.01)

(52) U.S. Cl.
USPC .................. 435/4; 977/701; 977/774; 506/12

(58) Field of Classification Search
None
See application file for complete search history.

(56) References Cited

U.S. PATENT DOCUMENTS

| | | | |
|---|---|---|---|
| 6,274,323 B1 | 8/2001 | Bruchez et al. | |
| 6,306,610 B1 * | 10/2001 | Bawendi et al. | 435/7.1 |
| 6,379,622 B1 | 4/2002 | Polak et al. | |
| 6,514,784 B1 | 2/2003 | Dubowski | |
| 6,770,441 B2 | 8/2004 | Dickinson et al. | |
| 7,755,080 B2 * | 7/2010 | Song et al. | 257/22 |
| 2002/0028457 A1 | 3/2002 | Empedocles | |
| 2002/0123227 A1 * | 9/2002 | Winningham et al. | 438/700 |

OTHER PUBLICATIONS

Han et al (2001 Nature Biotechnology 19:631-635).*
Chee et al (1996 Science 274:610-614).*
Bagwe et al., "Bioconjugated Luminescent Nanoparticles for Biological Applications," Journal of Dispersion Science and Technology, vol. 24, Nos. 3 & 4, 2003, pp. 453-464.
Lefebvre et al., "Tunable Emission from InAs Quantum Dots on InP Nanotemplates," J. Vac. Sci. Technol. B 20(5), American Vacuum Society, Sep./Oct. 2002, pp. 2173-2176.
Jovin, "Quantum Dots Finally come of Age," Nature Biotechnology, vol. 21, Jan. 2003, pp. 32-33.
Dubowski et al., "Laser-Induced InAs/GaAs Quantum Dot Intermixing," Applied Physics Letters, vol. 77, No. 22, Nov. 27, 2000, pp. 3583-3585.
Parak et al., "Labelling of Cells with Quantum Dots," IOP Publishing Ltd, Nanotechnology 16, Jan. 25, 2005, R9-R25.
Adlkofer et al., "Enchancement of Photoluminescence from Near-Surface Quantum Dots by Suppression of Surface State Density," Phys. Chem. Chem. Phys., 2002, 4, pp. 785-790.
Peng et al., "Epitaxial Growth of Highly Luminescent CdSe/CdS Core/Shell Nanocrystals with Photostability and Electronic Accessibility," Journal of the American Chemical Society, New York, vol. 119, Jan. 1, 1997, pp. 7019-7029.
Michalet et al., "Quantum Dots for Live Cells, in Vivo Imaging, and Diagnostics", NIH Public Access Science, Jan. 28, 2005, No. 307, pp. 538-544.

* cited by examiner

*Primary Examiner* — Christopher M Gross
(74) *Attorney, Agent, or Firm* — Fay Kaplun & Marcin, LLP

(57) ABSTRACT

A method and a device for detecting the presence of a predetermined substance, in which a quantum dot is produced on a substrate. The quantum dot emits a radiation at a predetermined wavelength, and is covered with a surface layer to which the predetermined substance attaches. A deviation of the value of a parameter related to the radiation is produced when the predetermined substance attaches to the surface layer. This deviation can be detected to thereby sense the presence of the predetermined substance.

11 Claims, 8 Drawing Sheets

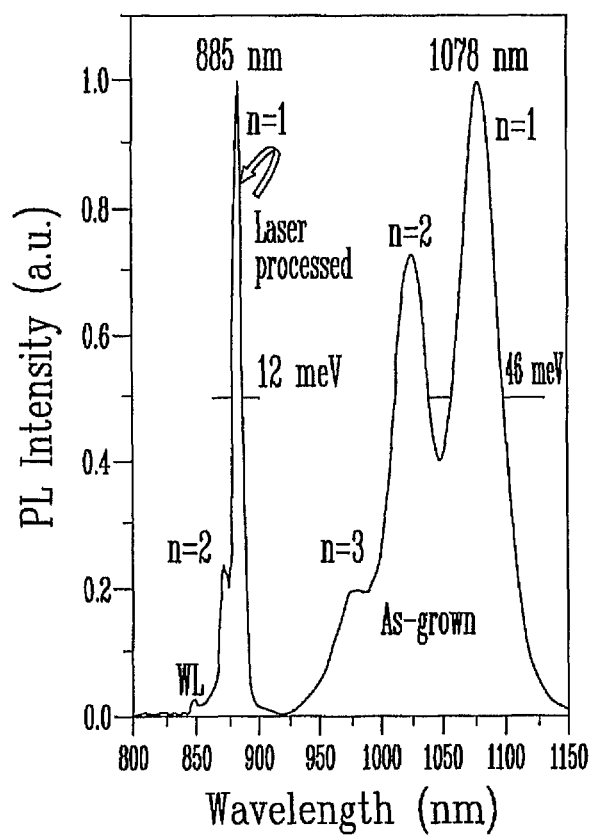
FIG_2

QUANTUM DOT TEMPLATE FOR FAST AND SIMULTANEOUS DETECTION OF DIFFERENT INFECTIOUS AGENTS

The present application was filed May 29, 2008 and is a 371 of PCT/CA06/00367 filed Mar. 10, 2006 which claims benefit of provisional application 60/659,872 filed Mar. 10, 2005.

FIELD OF THE INVENTION

The present invention relates to a method and device for detecting the presence of a predetermined substance by means of at least one quantum dot. More specifically, but not exclusively, the present invention relates to a method and device using quantum dot array(s) for simultaneously detecting different substances such as, for example, biomolecules, pathogens or the like.

BACKGROUND OF THE INVENTION

Bright photoluminescence (PL) and small dimensions (typical diameter smaller than 20 nm) of semiconductor nanocrystals, also referred to as quantum dots (QDs), have led to a significant interest in this material as an attractive replacement for organic dye fluorescent probes used in biomolecular detection and cellular imaging [T. Jovin; "*Quantum dots finally come of age*", Nature Biotechnol. 21, 32 (2003)]. Commercially available colloidal QDs, such as CdSe capped with ZnS and encased in biocompatible shells, emit in the wavelength range of 400-650 nm depending on the QD diameter. A cap layer applied to the QD will play the role of passivating the QD surface and reduce the concentration of non-radiative recombination centers, the latter being responsible for quenching the PL radiation. However, the intensity of the PL radiation decreases with increasing thickness of the cap layer. Thus, it is of practical interest to develop QD surface passivation methods using thin cap layers, ultimately made of monolayers of a specific material. Materials that, in addition to the QD surface passivating feature, could be used as anchors for conjugating targeted biomolecules are also of interest. This is currently a subject of investigation in many laboratories.

Current specimen preparation schemes utilize water-soluble nanocrystals, i.e. "free-standing" QDs. Generally speaking, quenching of the luminescence radiation in unpassivated semiconductor nanocrystals as well as the little-understood surface chemistry of these particles have been key issues that limited the quest for the QD-based biodiagnostics. An example of unwanted properties of free-standing QDs is their intermittent PL, known as 'blinking' [R. P. Bagwe et al.: "*Bioconjugated Luminescent Nanoparticles for Biological Applications*", J. Disp. Sci. Technol. 24, 453 (2003)]. Free-standing QDs do not yield emission/fluorescence spectra sufficiently narrow to make them available for simultaneous recognition of many different biomolecules. Practically, with this approach, it would be difficult to work with more than 10 color-tagged different biomolecules. Also, the study of biological systems in-vivo would require QDs emitting in the wavelength range of 800-1100 nm, which corresponds to the minimal optical absorption of combined blood, tissue and water (biological "optical window"). Such materials have yet to be developed.

In summary, difficult-to-implement technologies of compound semiconductors, problems with controlling the size, shape and uniformity of nanocrystals needed for achieving high accuracy testing and bright luminescence from QD containing biological assays, as well as the not well understood chemistry of QD surfaces have hindered the progress in the area of colloidal QD-based biodetection.

SUMMARY OF THE INVENTION

To overcome the above-discussed problems and drawbacks, there is provided, in accordance with the present invention, a method for detecting the presence of a substance by producing, on a substrate, a quantum dot which emits a radiation at a predetermined wavelength. The quantum dot is covered with a surface layer to which the predetermined substance attaches and produces a deviation of the value of a parameter related to the radiation when the predetermined substance attaches to the surface layer.

Also according to the present invention, there is provided a method for detecting the presence of a predetermined substance by producing, on a substrate, a quantum dot which emits a radiation at a predetermined wavelength. The quantum dot is covered with a surface layer, of which a predetermined area is processed to enable the predetermined substance to attach thereto and to produce a deviation of the value of a parameter related to the radiation when the predetermined substance attaches to said predetermined area.

Also according to the present invention, there is provided a method for detecting the presence of a plurality of predetermined substances by producing, on a substrate, an array of quantum dots which are processed to emit radiations at predetermined wavelengths respectively. The quantum dots are covered with a surface layer, of which predetermined areas are processed to enable the predetermined substances to selectively attach to at least one of the predetermined areas and to produce a deviation of the value of a parameter related to at least one of the radiations from the quantum dots when at least one of the predetermined substances attaches with at least one of the predetermined areas.

According to the present invention, there is provided furthermore a device for detecting the presence of a predetermined substance that comprises a quantum dot produced on a substrate and covered by a surface layer. The quantum dot emits radiation at a predetermined wavelength and the surface layer is structured to attach the predetermined substance and produce a deviation of the value of a parameter related to the radiation when the predetermined substance attaches to the surface layer.

Also according to the present invention, there is provided a device for detecting the presence of a predetermined substance that comprises a quantum dot produced on a substrate and covered by a surface layer. The quantum dot emits a radiation at a predetermined wavelength and the surface layer comprises a predetermined area that is processed to enable the predetermined substance to attach thereto and to produce a deviation of the value of a parameter related to the radiation when the predetermined substance attaches to the predetermined area.

According to the present invention, there is provided finally a device for detecting the presence of a plurality of predetermined substances that comprises an array of quantum dots produced on a substrate and covered by a surface layer. The quantum dots are processed to emit radiations at predetermined wavelengths respectively and the surface layer comprises predetermined areas processed to enable the predetermined substances to selectively attach to at least one of the predetermined areas and to produce a deviation of the value of a parameter related to at least one of the radiations from the quantum dots when at least one of the predetermined substances attaches with at least one of the predetermined areas.

The foregoing and other objects, advantages and features of the present invention will become more apparent upon reading the following non restrictive description of illustrative embodiments thereof, given by way of example only with reference to the accompanying drawings.

BRIEF DESCRIPTION OF THE DRAWINGS

In the appended drawings:

FIG. 1d is a cross sectional elevation view of a substrate with a multicolor linear array of QDs covered by a cap layer and a surface passivation layer with functionalized predetermined areas being attaching or trapping substances such as biomolecules, pathogens or the like;

FIG. 2 is a graph showing an example of PL spectra measured from an InAs/GaAs QD material;

FIG. 4b schematically illustrates a cleaving process in a solution applied to the crystal wafer of FIG. 4a;

DETAILED DESCRIPTION

The non-restrictive illustrative embodiments of the method and device according to the present invention will now be described.

In general terms, the non-restrictive illustrative embodiments relates to a Quantum Dot template provided with an array or multiple arrays of QDs for example multicolor array(s) of QDs. As will be described in the following description, the multicolor array(s) of QDs can been selectively processed to allow the simultaneous detection of different substances, such as biomolecules, pathogens or the like. More specifically, a 2-dimensional array of QDs is used for detecting biomolecules that could attach themselves to the QD surface. The optical emission (photoluminescence) of a QD immobilized on the substrate could be used to monitor the presence of a specific biomolecule attached to QD in the same way as, e.g., human bones could be seen in a patient exposed to an x-ray radiation. This is possible due to the fact that the QD diameter, which is typically less than 20 nm, is significantly smaller that that of a virus (100-200 nm) or other pathogenic biomolecules. Thus, the QD radiation (intensity and/or wavelength) is expected to be modified by trapped bio-molecules. In addition, it is possible that the modification of QD photoluminescence could be related to the electric charge carried out by a targeted biomolecule via the surface band bending process, resonant absorption (emission), etc.

The structure of one embodiment of the device according to the present invention will now be described with reference to FIGS. 1a-1d. The method according to this embodiment will be simultaneously described.

Figure 1A:
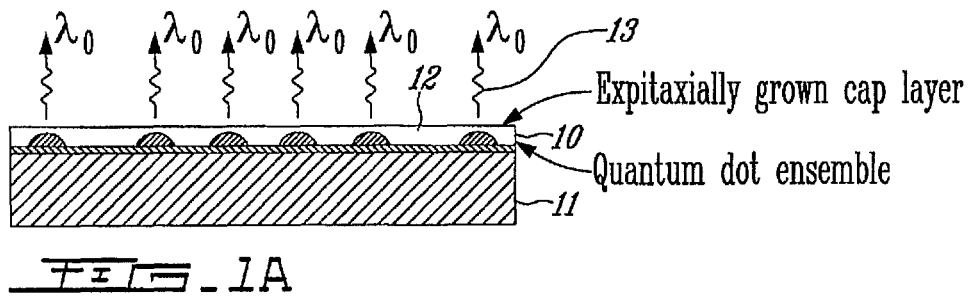
FIG. 1a is a cross sectional elevation view of a substrate with a mono-color array of QDs covered with a cap layer.

Referring to FIG. 1a, a substrate 11 is first provided. The substrate 11 can be made of any suitable material, for example a one-element semiconductor (Si, Ge, etc.) or compound semiconductor (GaP, GaAs, InP, InAs, etc). Of course, any other types of suitable substrate materials can also be contemplated.

Still referring to FIG. 1a, an array of QDs such as 10 are grown on the substrate 11. As an example, the QDs can be made of a semiconductor material such as InAs/GaAs, CdSe/ZnS, etc.

As known to those of ordinary skill in the art, the material forming the QDs 10 can be grown on one face of the substrate 11 using conventional techniques, for example molecular beam epitaxy, chemical beam epitaxy, etc. Also, to overcome at least some of the key technological problems related to the application of free-standing QDs to bio-detection, different arrays of QDs can be grown directly on different substrates through, for example, thin film deposition. Arrays of QDs could also be prepared by self-assembled growth and/or epitaxy on patterned wafers (substrates) [Lefebvre et al.: "*Tunable emission from InAs quantum dots on InP nanotemplates*", J. Vac. Sci. Technol B20, 2173 (2002)]. Such microstructures allow for implementation of various material processing techniques, such as tuning the QD emission wavelength, that would otherwise be impractical for colloidal QDs.

Still referring to FIG. 1a, a cap layer 12, made for example of InAs, can be epitaxially grown on the array of QDs 10.

Typically, measurement of PL radiation from two-dimensional (2D) arrays of QDs can be carried out by exciting the QD(s) with a laser spot exceeding the size of an individual QD. The non-QD material, however, will emit a radiation at a distinctly different wavelength, and at a much lower intensity than that of the QDs. As illustrated in FIG. 1a, every QD 10 of the array emits a radiation such as 13 at a wavelength $\lambda \cong \lambda_0$.

Figure 1B:
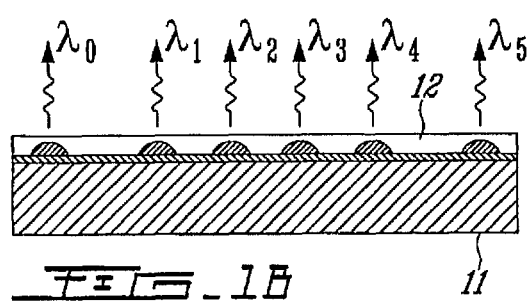
FIG. 1b is a cross sectional elevation view of a substrate with a multicolor linear array of QDs covered with a cap layer.

A laser-based technique can be used for tuning the PL radiation wavelength and characteristics of selected QDs or groups of QDs. More specifically, laser-based techniques can be used to produce a multicolor linear array of QDs 10 as shown in FIG. 1b. To achieve production of a multicolor linear array, the QDs can be processed through known laser-based lithography techniques such as infrared (IR) laser-based QD intermixing, UV laser-based bandgap engineering as described in U.S. Pat. No. 6,514,784, or other methods of quantum well intermixing, such as those based on ion-implantation. Depending on the concentration of QDs, and resolution of the laser-based lithography technique, an individual bio-pixel can be linked with either one QD or a group of QDs. As illustrated in FIG. 1b, the QDs of the resulting multicolor linear array could emit PL radiation at different wavelengths $\lambda_0$, $\lambda_1$, $\lambda_2$, $\lambda_3$, $\lambda_4$ and $\lambda_5$, respectively. This technique overcomes one of the limitations of the conventional techniques for fabricating 2D arrays of QDs, which is the inability to fabricate multicolor arrays of QDs. Using these conventional techniques, all the QDs from a single wafer emit PL radiation at a single, specific nominal wavelength.

Figure 1C:
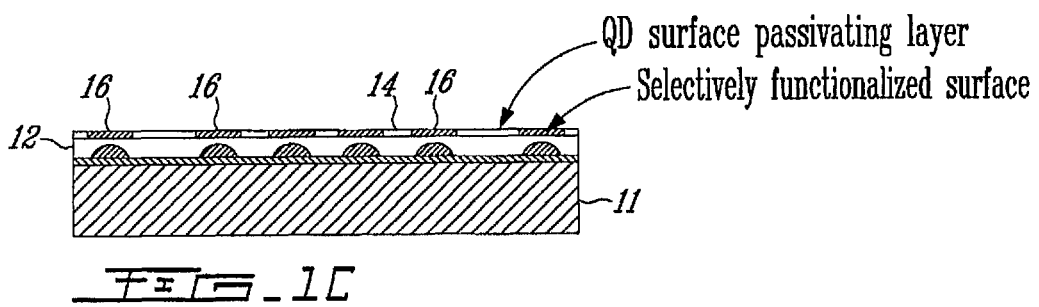
FIG. 1c is a cross sectional elevation view of a substrate with a multicolor linear array of QDs covered by a cap layer and a surface passivation layer with functionalized predetermined areas.

Referring now to FIG. 1c, a QD surface passivating layer 14, made for example of thiol or $SiO_2$, is grown on the cap layer 12. Layer 14 is selectively functionalized by laser-controlled surface chemistry to form predetermined areas such as 16 covering the respective QDs. More specifically, the predetermined areas 16 are processed to make them capable of trapping or attaching a predetermined substance, for example a specific type of substance 15, such as a biomolecules, a pathogen or the like. An alternative to laser-controlled surface chemistry is to use selective area deposition on the cap layer 12 or the functionalization layer 14 of a material that could attach or trap, for example an antibody material capable of trapping or attaching a specific type of biomolecule 15.

Figure 1D:
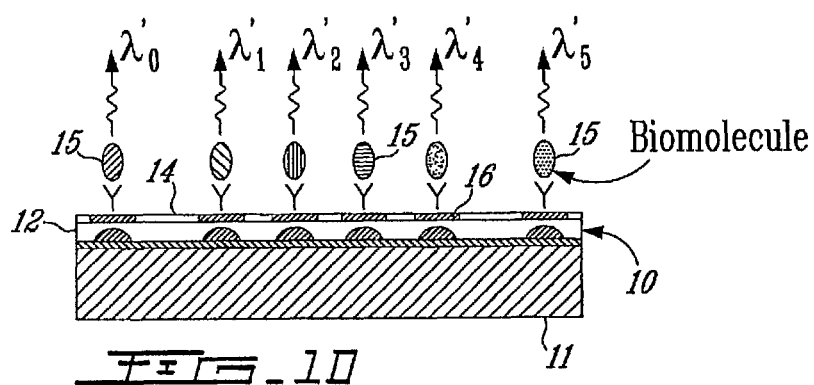

Referring now to FIG. 1d, the presence of different substances, for example different biomolecules, pathogens or the like can be detected simultaneously by monitoring optical properties of the QDs 10, for example a deviation of photoluminescence intensity and PL wavelength.

Using the above principles, it is possible to build a QD template (QD-T) comprising closely-spaced multicolor linear arrays of QDs. Compared to existing systems, this template will have a far greater number of simultaneously resolvable QDs' PL radiation distinct spectra designed for ultra-sensitive detection of minuscule quantities of different substances, for example biomolecules, pathogens or the like.

Different substances such as biomolecules, pathogens or the like, when attached or trapped on the functionalized predetermined areas 16, will have different effects on the optical properties of the QDs, in particular on the QD spectroscopy including photoluminescence intensity and PL wavelength. Detection of different substances, such as biomolecules, pathogens or the like, when carried out with a mono-color array of QDs, would be limited to a restricted number of different substances within a small area. An array of QDs emitting PL radiation at various wavelengths would greatly increase the number of different substances, such as biomolecules, pathogens or the like, that can be detected. Monitoring of parameters such as the deviation of photoluminescence intensity and PL wavelength through the different areas 16 modified by the presence of trapped substances such as biomolecules, pathogens or the like will also provide information required for the identification of a pathogen of interest. In order to detect different substances, such as biomolecules, pathogens or the like on a same QD array, the array can be selectively processed in different areas, so different substances, such as biomolecules, pathogens or the like could be attached or trapped in these areas. Multi-substance detection will be achieved by mapping parameters such as the deviation of photoluminescence intensity and PL wavelength. Detection of one biomolecule attached to the surface of QD would be possible with a probe beam diameter comparable to that of the cross-section of the biomolecule (d≈0.2 micrometer).

According to an example related to the alternative consisting of selective area deposition on the cap layer 12 or the passivating layer 14 of a material, binding commercially available monoclonal antibodies to separate dots in linear arrays of QDs would enable simultaneous detection of hundreds of viruses or viral antigens. In addition, patient antibodies to commercially available viral antigens could also be detected in a similar fashion.

According to another example, the surface of a QD array covered with an antibody can serve to detect antibody-matching pathogen such as bacteria, spore, virus, toxin, etc. Such QD array could also be used for monitoring cell and neuron interaction/behaviour, fast drug screening, etc. The presence of bacteria, or other pathogen, in a specific area of the wafer can be detected by measuring a deviation of photoluminescence intensity and PL wavelength of the QD of concern. Monitoring of parameters such as the deviation of photoluminescence intensity and PL wavelength through the areas modified by the presence of trapped pathogens will also provide information required for the identification of a pathogen of interest. In order to detect several pathogens simultaneously on a same QD array, the array can be selectively processed in different areas, so different antibodies could be attached or trapped in these areas. Multi-pathogen detection will be achieved by mapping parameters such as the deviation of photoluminescence intensity and PL wavelength.

FIG. 2 shows an example of PL spectra measured from an InAs/GaAs QD material. More specifically, FIG. 2 illustrates a PL spectra measured at two sites 4 mm apart from each other on a same sample corresponding to the as-grown InAs/GaAs QD material (long-wavelength spectrum) and the laser-processed material blueshifted by 251 meV. As can be seen in FIG. 2, the QD spectrum dominates the signal and only a small PL contribution from the background material, indicated as WL, is observed in that case (J. J. Dubowski et al., Appl. Phys. Lett. 77, 3583 (2000)).

According to non-restrictive illustrative embodiments:
The QD template may comprise a plurality of substrates on which one or many arrays of QDs can be grown.
A complete array or complete arrays of QDs can be used to detect a single given substance.
In an array, each single QD can be used to detect a respective substance through an associated functionalized predetermined area whereby such an array can be used to detect a large quantity of different substances such as biomolecules, pathogens or the like.
The QDs of an array or a plurality of arrays can be divided into groups of QDs each detecting a particular substance through respective functionalized predetermined area(s).
The arrays of QDs can be linear or present any other geometric configuration.
Etc.

A method to increase both detection sensitivity and reproducibility of the fabrication of a device according to the present invention will now be described. More specifically, the following four technological problems 1, 2, 3 and 4 will be addressed.

1. Intensity of the PL radiation decreases with increasing thickness of the cap layer surrounding the QD.

Intensity of the PL radiation from a 20 nm diameter QD is expected to be altered by a virus or other biomolecule of 100 nm in diameter, or larger, that are trapped on the surface of cap layer.

The alteration of the PL intensity mentioned in the preceding paragraph could be due to physical attenuation of the signal, band bending of the surface induced by an electric charge, etc.

Typical thickness of a cap layer surrounding a free-standing QD, such as a cap layer made of ZnS on a QD made of CdSe, is about 2-3 nm. But, fabrication of wafers with 2D arrays of QDs having thin caps, e.g. a cap layer made of GaAs on a QD made of InAs, is a complicated issue. Often PL radiation cannot be even measured if the cap layer thickness is 6 nm and les [K. Adikofer et al., Phys. Chem. Chem. Phys. 4, 785-790 (2002)]. On the other hand, an excessive distance between the QD and a trapped substance such as biomolecules, pathogens or the like reduces the chances for a successful detection based on the QD spectroscopy including photoluminescence intensity and PL wavelength. To solve this problem, it is proposed to functionalize sides of freshly etched ridges with QDs. The idea is illustrated in FIGS. 3a and 3b.

Figure 3A:
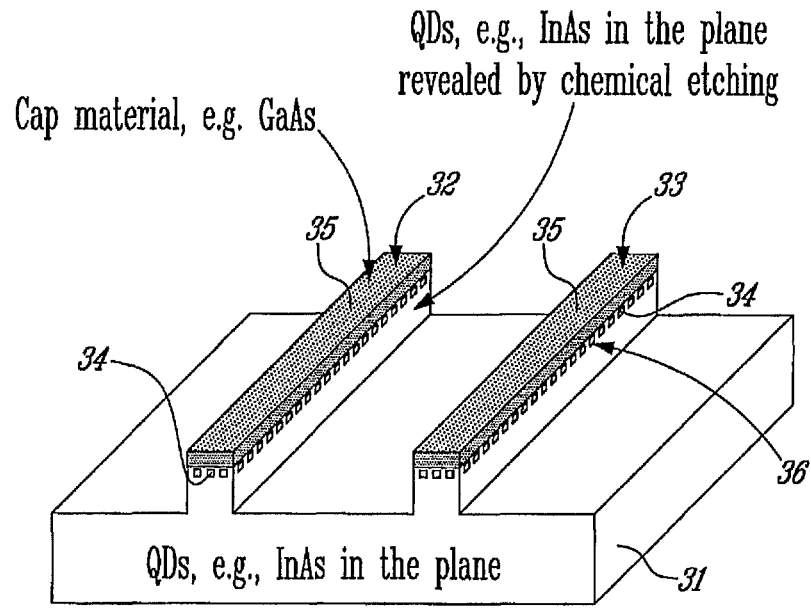
FIG. 3a is a perspective view of ridge microstructures etched to expose or reveal a fresh surface of QDs.

As illustrated in FIG. 3a, ridge microstructures 32 and 33 are etched to reveal a plane of a fresh surface such as 34 of QDs that are not easily accessible for interfacing through the cap layer such as 35. In the example of FIG. 3a, the substrate 31 is made of GaAs, the cap layers 35 are made of GaAs and the QDs such as 36 are made of InAs.

Figure 3B:
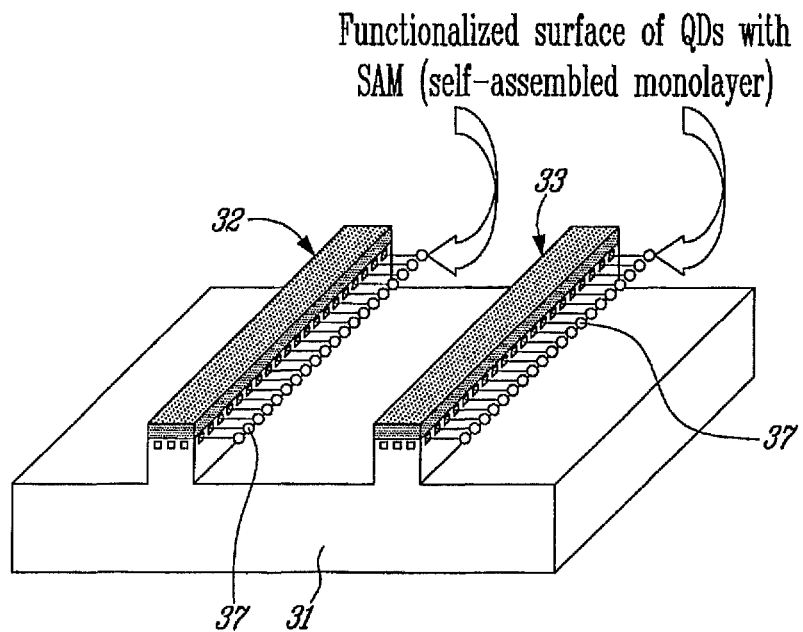
FIG. 3b is a perspective view of ridge microstructures etched to reveal a fresh surface of QDs functionalized with a pathogen specific self-assembling monolayer.

Referring now to FIG. 3b, the newly revealed fresh surface such as 34 of the QDs 36 is functionalized in the plane of etching with a pathogen specific (SAM) self-assembling monolayer 37.

In order to reduce the probability of surface contamination, the process of ridge etching could be carried out in-situ along with the surface functionalization step.

2. Atomically clean surfaces of binary, ternary or quaternary semiconductor materials used in the fabrication of QD microstructures, which allow for reproducible attachment of substances such as biomolecules, pathogens or the like, are difficult to achieve.

This problem is well known in the epitaxial growth of thin films. Fabrication of an atomically clean surface requires special chemical cleaning procedures. However, chemical treatment leads to deviations from stoichiometry and, consequently, to difficulties in controlling surface reactions. On the other hand, it is well known that crystals with cubic symmetry can be relatively easily cleaved along some of their crystallographic planes.

Figure 4A:
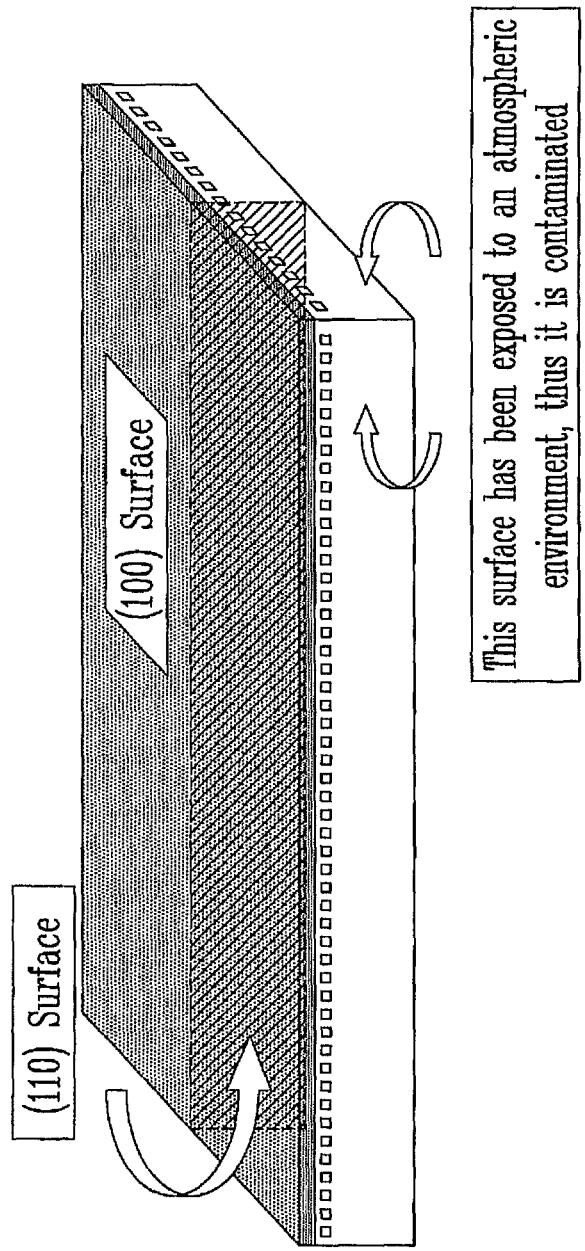
FIG. 4a is a perspective view of a crystal wafer showing (100) and (110) planes.
Figure 4B:
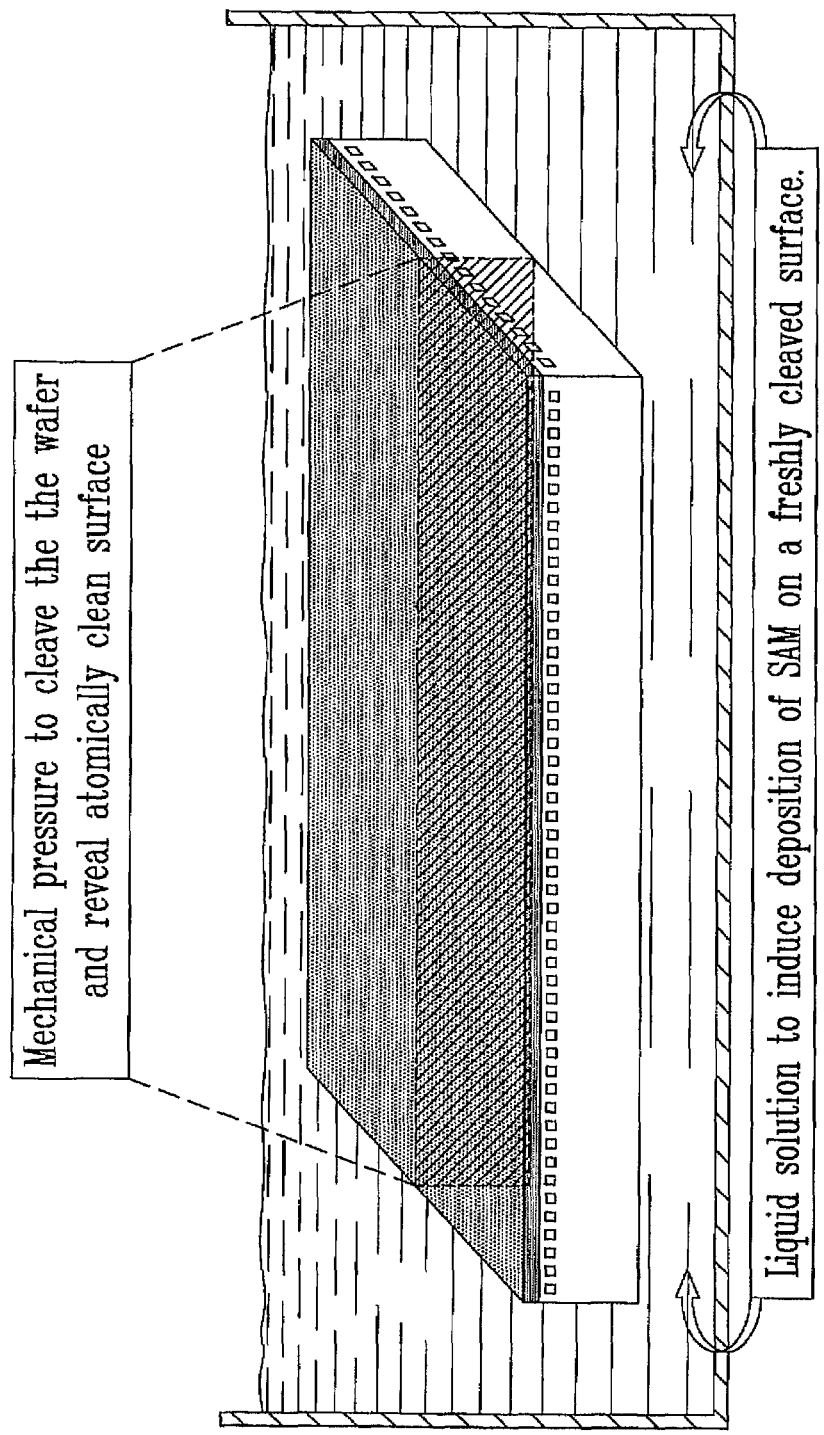
Figure 4C:
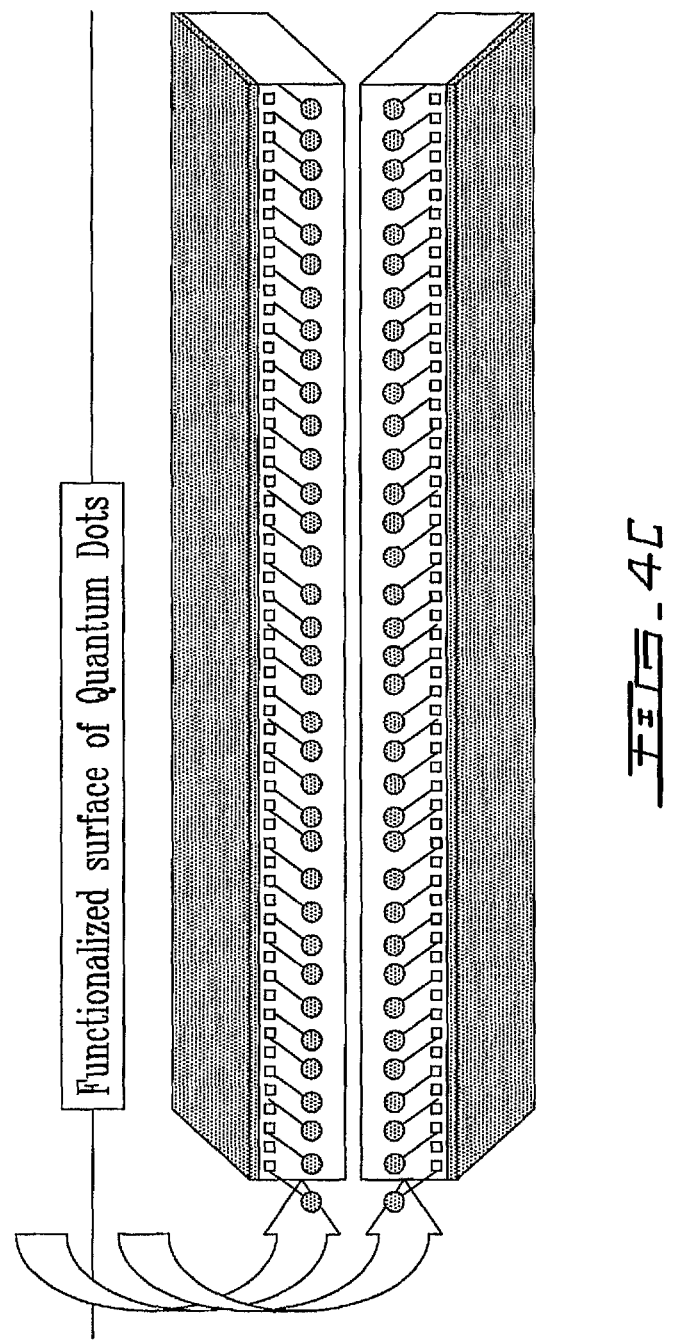
FIG. 4c is a perspective view showing a functionalized cleaved surface of QDs of the wafer of FIGS. 4a and 4b.

For example, as illustrated in FIG. 4a, the (110) plane, which is oriented perpendicularly with respect to the (100) plane (growth plane of QDs), is a natural cleavage plane used for laser mirror fabrication in GaAs and in P material systems. This feature can be used to reveal surfaces with QDs for in-situ functionalization. The wafer cleaving process could be carried out in a liquid solution 41 (FIG. 4b) of chemicals required for deposition of different SAM, such as thiols comprising —$NH_2$ terminal group (FIG. 4c). Cleaving in vacuum and deposition of SAMs is also possible with this approach, but likely this would be a less economically viable solution. For typical QD densities achieved with current growth technologies, there would be a minimum of 10 QDs in each 1-micrometer long edge revealed by cleaving the QD wafer.

3. Bio-detection using a 2D array of QDs (detection of viruses of the same type).

Figure 5A:
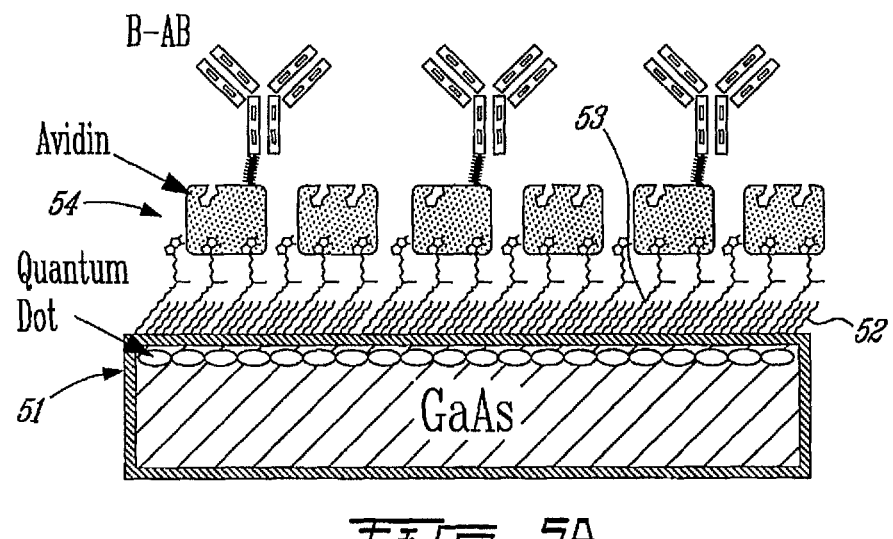
FIG. 5a schematically illustrates a quantum dot array which has been bio-functionalized with a thiol-biotin-avidin architecture.
Figure 5B:
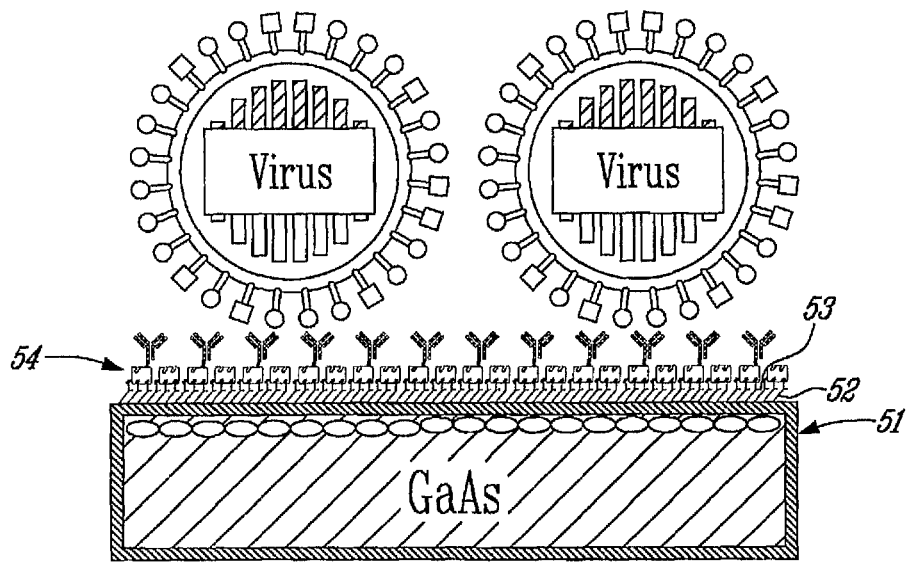
FIG. 5b schematically illustrates the quantum dot array as of FIG. 5a, in which some viruses are attached to the quantum dot array.

FIGS. 5a and 5b show a 2D array of quantum dots 51 presenting a bio-architecture on its top surface. More specifically, a thin cap layer 52 covering the quantum dots 51 is functionalized for predetermined areas of the wafer to enable the attachment of specific antibodies. More specifically in FIGS. 5a and 5b, the top surface 53 of the QD template is bio-functionalized. A similar bio-functionalization step could be carried out on an etched or cleaved surface with QDs as in FIGS. 3a, 3b, 4a, 4b or 4c. On FIG. 5a, the bio-functionalization is achieved by using a thiol-biotin-avidin architecture 54. However, there exist other options, such as attaching antibodies or functionalized DNA to the surface by means of biotin or avidin.

Figure 6A:
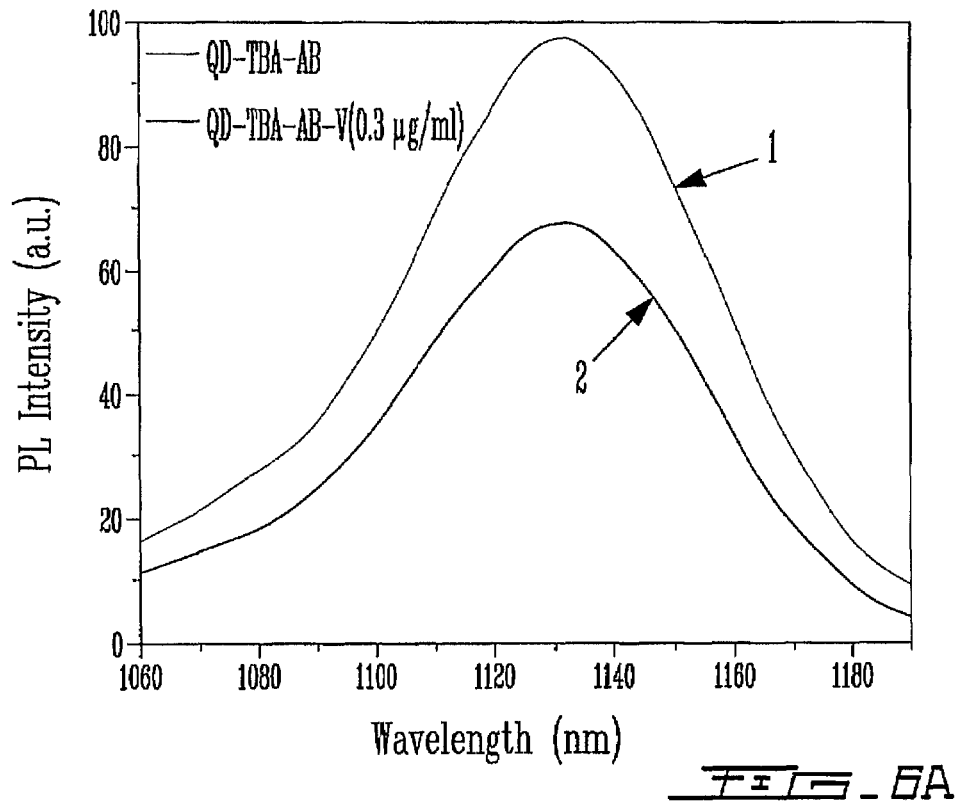
FIG. 6a is a graph showing QD PL spectra before and after a bio-functionalized QD array has been exposed to Influenza A viruses.
Figure 6B:
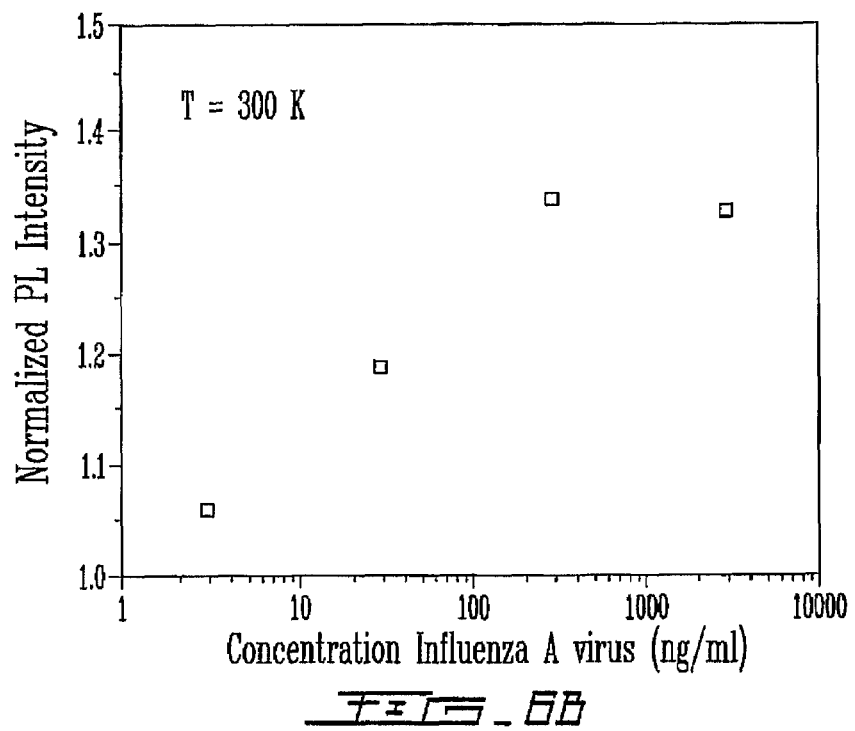
FIG. 6b is a graph showing bio-detection of an Influenza A virus concentration as low as 3 ng/ml.

FIG. 6a compares the photoluminescence spectrum of a QD array which is bio-functionalized with Influenza A respectively before and after it has been exposed to the Influenza A virus (respectively curve 2 and curve 1 in FIG. 5a). It can be seen that the attachment of viruses in this case has resulted in an increase of about 50% of the QD PL radiation measured at 1130 nm. FIG. 6b shows that with this approach, a detection of the Influenza A virus could be carried out for virus concentrations as low as 3 ng/ml. It has to be noted, however, that these measurements have been carried out with a laser probing beam of a diameter of approximately 20 micrometers. This means that a significant contribution to the PL radiation originated from the virus-free surface. Reducing the diameter of the probing beam to about 1 micrometer, i.e. to a cross-section area comparable to that of a virus, is expected to drastically improve the sensitivity of these measurements. Also, a sub-micrometer diameter probing beam is expected to provide advantageous conditions for probing QD photoluminescence from the side of etched or cleaved wafers like those that are shown in FIGS. 3a, 3b, 4a, 4b and 4c.

4. Single biomolecule detection and multi-pathogen detection.

The ability to probe QD PL radiation from the surface occupied by an individual virus, pathogen or biomolecule, and the drastically different PL radiation from QDs that have not been affected by such a virus, pathogen or biomolecule, ultimately offers detection at the single biomolecule level. Probing with sub-micrometer diameter beam could be applied to a sensor comprising hundreds of bio-pixels with different antibodies. In this way, a 5 mm×5 mm sensor could be armed with different antibodies to detect at least 100 different pathogens.

Although the present invention has been described hereinabove by way of non-restrictive illustrative embodiments thereof, these embodiments can be modified at will within the scope of the appended claims without departing from the spirit and nature of the subject invention.

What is claimed is:

1. A device for detecting a presence of a predetermined substance in a liquid, comprising:
 a substrate;
 an epitaxial quantum dot directly on a face of the substrate, the quantum dot emitting a radiation at a predetermined wavelength; and
 passivating layers including a cap covering the quantum dot, structured to attach the predetermined substance and produce a deviation of a value of a parameter related to the radiation when the predetermined substance attaches to a portion of the passivating layers.

2. The device as recited in claim 1, further comprising a detector of the deviation to detect the presence of the predetermined substance.

3. The device as recited in claim 1, wherein the parameter is the wavelength of the radiation.

4. The device as recited in claim 1, wherein the quantum dot comprises a surface revealed by etching, and wherein at least a portion of the passivating layers cover the revealed surface.

5. The device as recited in claim 1, wherein the quantum dot comprises a surface revealed by cleaving, and wherein at least a portion of the passivating layers cover the revealed surface.

6. The device as recited in claim 1, wherein the predetermined substance is selected from the group consisting of biomolecules, pathogens, spores, toxins, viruses, and bacteria.

7. The device as recited in claim 1, wherein the quantum dot is produced using an epitaxial growth process.

8. The device as recited in claim 7, wherein the epitaxial growth process comprises molecular beam epitaxy.

9. The device as recited in claim 1, further comprising a plurality of quantum dots forming an array.

10. The device as recited in claim 1, further comprising a plurality of quantum dots forming a two-dimensional array.

11. The device as recited in claim 7, wherein the epitaxial growth process comprises chemical beam epitaxy.

* * * * *